United States Patent [19]
Pentoney, Jr. et al.

[11] Patent Number: 5,143,850
[45] Date of Patent: Sep. 1, 1992

[54] DETECTION OF RADIOISOTOPE LABELED COMPONENTS IN A CAPILLARY

[75] Inventors: Stephen L. Pentoney, Jr., Yorba Linda; Richard N. Zare, Stanford, both of Calif.

[73] Assignee: Beckman Instruments, Inc., Fullerton, Calif.

[21] Appl. No.: 557,439

[22] Filed: Jul. 23, 1990

[51] Int. Cl.$^5$ .............. G01N 23/00; G01N 33/00; C25B 1/00
[52] U.S. Cl. .............................. 436/57; 436/88; 436/147; 204/182.8; 204/299 R
[58] Field of Search .................. 436/57, 88, 147; 204/182.8, 299 R

[56] References Cited

U.S. PATENT DOCUMENTS

| | | | |
|---|---|---|---|
| 4,389,670 | 6/1983 | Davidson et al. | 358/111 |
| 4,769,334 | 9/1988 | Fleming | 436/57 |
| 4,816,123 | 3/1989 | Ogan et al. | 204/183.3 |
| 4,852,137 | 7/1989 | Mackay | 378/62 |
| 4,865,706 | 9/1989 | Karger et al. | 204/182.8 |
| 4,892,638 | 1/1990 | Watanabe et al. | 204/299 |
| 4,966,854 | 10/1990 | Fleming | 436/57 |

FOREIGN PATENT DOCUMENTS

| | | |
|---|---|---|
| 0198403 | 10/1986 | European Pat. Off. . |
| 0240728 | 10/1987 | European Pat. Off. . |
| 0304295 | 2/1989 | European Pat. Off. . |
| 0361750 | 4/1990 | European Pat. Off. . |
| 3812899 | 10/1989 | Fed. Rep. of Germany . |

OTHER PUBLICATIONS

Bittner et al; "Electrophoretic Transfer of Proteins and Nucleic Acids from Slab Gels to Diazobenzyloxymethyl Cellulose of Nitrocellulose Sheets"; *Analytical Biochemistry* 102, 459-471 (1980).

Publication by Photometrics Ltd., "Charge-Coupled Device for Quantitative Electronic Imaging", pp. 1-28, 1989.

Sales brochure by Photometrics Ltd.

Reprint from American Laboratory, "Channel Electron Multipliers", Mar. 1979.

Derenzo, Stephen E.; "Gamma-Ray Spectroscopy Using Small Cooled Bismuth Germanate Scintillators and Silicon Photodiodes"; *Nuclear Instruments and Methods in Physics Research* 219 (1984) pp. 117-122.

Burolla, Victor P., Pentoney, Stephen L., Jr., and Zare, Richard; Reprint from American Biotechnology Laboratory, "High Performance Capillary Electrophoresis", Nov./Dec. 1989.

Jorgenson, James W. and Lukacs, Krynn DeArman, "Capillary Zone Electrophoresis"; *Science*, vol. 222, (Oct. 21, 1983) pp. 266-272.

Kianiansky, D. et al; "On-Line Radiometric Detection In Capillary Isotachophoresis"; *Journal of Chromatography*, 258 (1983) 238-243.

*Primary Examiner*—John W. Rollins
*Attorney, Agent, or Firm*—William H. May; Paul R. Harder; Wen Liu

[57] ABSTRACT

A detection and quantification technique for radioisotope labeled components separated in a capillary separation channel. The section of the separation channel containing the separated components is significantly cooled to substantially eliminate diffusion of the components while detection is being carried out. The section can be frozen and autoradiography technique or solid state electronic imaging technique can be utilized to obtain an image representative of the relative amounts of separated components.

21 Claims, 2 Drawing Sheets

DETECTION OF RADIOISOTOPE LABELED COMPONENTS IN A CAPILLARY

BACKGROUND OF THE INVENTION

1. Field of the Invention

The present invention relates to analytical separation of samples into components in capillaries, and more particularly to the detection of the separated components which have been labeled by radioisotopes.

2. Description of Related Art

Analytical separation of components of a sample has widely been carried out using capillaries as separation channels. For example, capillary electrophoresis has proven useful as a highly efficient method for analytical separation of a minute amount of sample. In this process, an electric field is applied between the two ends of a capillary tube into which a buffer or electrolyte containing the sample is introduced. The electric field causes the components of the sample to migrate through the tube. The components will have different electrophoretic mobilities so that the components are resolved into zones or bands in the separation channel during migration through the channel.

Early in the development of capillary electrophoresis, it was noted that the successful detection of separated sample components present within the narrow confines of the capillary separation channel posed a major challenge. In response to this challenge, much research has been directed toward the development of sensitive and selective detectors for capillary electrophoresis. To improve selectivity of detection, it is desirable to employ detectors which respond only to certain sample components but not to others, thus permitting detection of the origin of certain sample components despite chemical changes and the presence of other components and substances. Since the amounts of materials used in capillary electrophoresis are so minute, detectors used must have high sensitivity. One way to increase detection selectivity and sensitivity is to label the sample components with one or more radioisotopes.

While state-of-the-art radiation detection technology offers extremely high sensitivity and selectivity in detection of sample components in the capillary separation channel, there are certain limitations. In the past, detection of radioisotope-labeled components within the capillary separation channel has been accomplished during electrophoretic separation. A radiation detector is placed along the capillary tube at a fixed location. The labeled components move past the detector at a finite velocity. This technique is referred to as "flow counting detection". The ability to accurately detect and quantify the components is dependent on the residence time of the components within the detection range of the detector and the zone broadening which occurs due to diffusion of the components in the separation channel. The residence time affects sensitivity and diffusion affects both resolution and sensitivity. While detection sensitivity can be improved by increasing the residence time of the components (for example, by reducing the applied electric potential to slow down or stop the flow in the separation channel), zone broadening caused by diffusion is more pronounced as residence time is increased thereby degrading the resolution. Hence, there is a trade-off between sensitivity and resolution in the flow counting approach of detection.

Sample zones are caused to broaden by at least two mechanisms. First, the applied electric field causes resistive Joule heating of the buffer to create a temperature gradient between the axis of the separation channel and the walls of the channel. This creates a convective recirculation within the channel thereby causing the sample zones to broaden. Second, there is a concentration gradient between the zones and the adjacent buffer which causes diffusion across the zone boundaries. Such diffusion is more pronounced at higher temperature.

While broadening of sample zones causes by convection can be reduced to some extent but not eliminated by effective heat dissipation through the surrounding capillary walls, longitudinal diffusion of sample components due to concentration differential is still present.

SUMMARY OF THE INVENTION

The present invention is directed to a technique for analyzing including detection and quantification of radioisotope-labeled sample components carried in a buffer solution or other separation medium in a capillary, wherein diffusion of the components is substantially eliminated. According to the present invention, the section of the capillary tube containing the separated sample components is significantly cooled to a temperature at which diffusion of the components is substantially eliminated. In one aspect of the present invention, the section of the capillary tube is cooled to a temperature at which the separation medium freezes. Detection of the separated components can be carried out for a prolonged period of time substantially without the adverse effect of diffusion. Hence, sensitivity of detection is substantially improved without compromising resolution.

In another aspect of the present invention, a radiation sensitive imaging device may be used to obtain an image representative of the spatial distribution and relative amounts of the components. The imaging device can be an x-ray film, photographic film, or a solid state imager such as a charge-coupled device. Penetrating radiation (such as high energy beta particles) may be directly detected or alternatively a scintillation material can be provided around or within the capillary separation channel for producing scintillation in response to radiation emitted from the radioisotope-labeled sample components. The photons produced from scintillation can be better detected by the imaging device for quantification of the sample components.

DESCRIPTION OF ILLUSTRATED EMBODIMENT

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
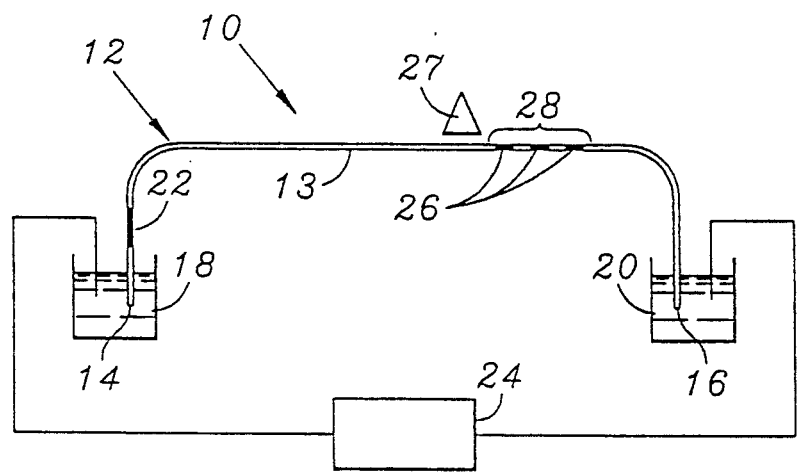
FIG. 1 is a schematic diagram of an electrophoretic separation system.

Referring to FIG. 1, an electrophoretic separation system 10 is schematically illustrated. The system 10 includes a fused silica capillary tube 12 defining a separation channel 13 with an inlet end 14 and an outlet end 16. An electrolyte buffer or other separation medium is supplied to the tube 12. The inlet end 14 is immersed in reservoir 18 and the outlet end 16 is immersed into another reservoir 20. A small volume of radioisotope labeled sample solution 22 is introduced into the inlet end 14 of the capillary tube 12. A high voltage is applied between the two reservoirs using a high voltage power source 24. Radioisotope labeled component molecules in the injected sample 22 then migrate at different rates along the length of the capillary separation channel under the action of the applied electric field. The sample is separated into its various components in zones 26 along the separation channel.

To create differential migration of sample components the separation channel may be filled with a stabilizing gel such as polyacrylamide. The use of gel-filled capillaries has been described for example in U.S. Pat. No. 4,865,706.

A detector 27 can be provided along the separation channel at a location where complete separation of the components is expected for detecting the general location of the separated components. Once the general locations of the separated components have been established, the electrophoretic separation process is halted by removing the applied high voltage. An autoradiographic technique is then applied to image the separated components. While autoradiography has been practiced in the past in connection with electrophoretic separation in gel slab, it has never been applied to capillary electrophoresis.

Shortly after the capillary electrophoretic separation process, at least the section 28 of the capillary tube 12 containing the separated sample components is placed in direct contact with an x-ray film (for example, Kodak® XAR-5 film) and frozen at −20° for a sufficiently long time period to allow detection of the radioisotope-labeled sample components. It may take as much as 15 hours or more for detection of the sample components which have been labeled with radioisotopes. Freezing of the contents in the section 28 of capillary tube significantly reduces zone broadening by longitudinal diffusion during the long exposure period of the x-ray film.

Figure 2:
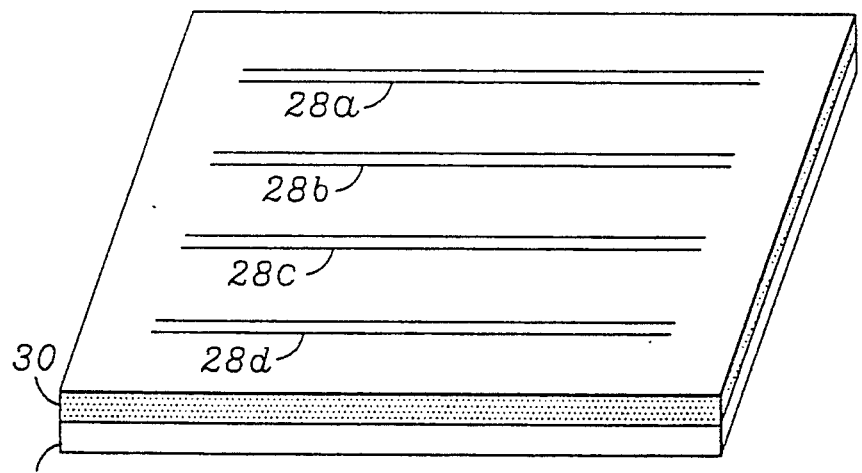
FIG. 2 is a diagram showing the arrangement for autoradiograph according to one embodiment of the present invention.

More particularly, the capillary tube section 28 is severed from the length of the capillary tube 12 and attached to a thick filter paper using cellophane tape. The filter paper provides a backing for easier handling of the short section 28. In certain applications in which the capillary tube section is not severed, the filter paper provides a backing for easier handling of the entire length of the capillary tube. Referring to FIG. 2, several sections 28a–d of capillary tube from several electrophoretic separations carried out at about the same time can be arranged in parallel on a filter paper 30. The filter paper 30 is laid on an x-ray film 32. The radiation from any one of the tube sections is not expected to affect the results of another section because of the high attenuation of the radiation. As a safeguard for the user against prolonged exposure to radiation, the filter paper 30 and film 32 are completely enclosed in a light-tight cassette (not shown) which may include a lead radiation shield. The cassette is placed in a cooling chamber at −20° C. for several hours to maintain the contents of the tube sections in a frozen state during exposure of the x-ray film.

Figure 3:
FIG. 3 is the reproduction of an x-ray film image of actual radioisotope-labeled sample components separated in a capillary tube.

This approach is applicable to the detection of sample molecules labeled with high energy beta or gamma emitting isotopes such as $^{32}P$ or $^{125}I$ or low energy alpha or beta emitting isotopes such as $^{3}H$, $^{14}C$, or $^{35}S$. FIG. 3 shows the image 40 of the spatial distribution of $^{32}P$ radioisotope-labeled components of a 40–60 mer poly d(A) sample in a polyacrylamide gel-filled capillary. The image 40 provides a qualitative comparison of the relative amounts of the sample components. It has been found that because high energy $^{32}p$ isotope emission is penetrable through the capillary wall, a scintillating material is not required to be used for imaging as would be in the case of low energy isotopes.

For low energy isotopes, because radioactive emissions are less penetrating through the walls of the capillaries, it is desirable to convert radioactive emissions to photons which are more penetrating through the capillary walls by means of scintillation. A scintillation material can be provided within the capillary separation channel as an integral part of the gel or electrolyte, or surrounding the separation channel as an integral part of the capillary wall. The use of scintillation material in a capillary for radioactivity detection has been described in a pending patent application Ser. No. 07/249,999 filed by the inventors of the present application along with other co-inventors. The scintillation material converts the less penetrating radiation into optical radiation which may easily pass through the capillary walls and sensitize a photosensitive film.

Alternative to photosensitive film, a solid state electronic imager such as a conventional charge-coupled device ("CCD") imager can be used to image the separated components. The CCD imager can integrate the number of photons emitted from scintillations over a period of time to quantify the relative amounts of separated components (the number of photons emitted from scintillation is proportional to the amount of components). The CCD imager can also provide an image of the spatial distribution of the separated components. A more detail discussion of a CCD scintillation detection system and its advantages is documented in copending U.S. patent application Ser. No. 07/533,976 by Jeff Quint entitled "Scintillation Detection Using Solid State Imager" which is commonly assigned to the assignee of the present invention and is incorporated herein by reference. The principles underlying CCD technology and the implementation of CCD technology have been documented by at least one CCD camera systems manufacturer and is familiar to one skilled in the art. See publication by Photometrics Ltd. entitled "Charge-Coupled Devices for Quantitative Electronic Imaging" (1989), which is incorporated herein by reference.

Figure 4:
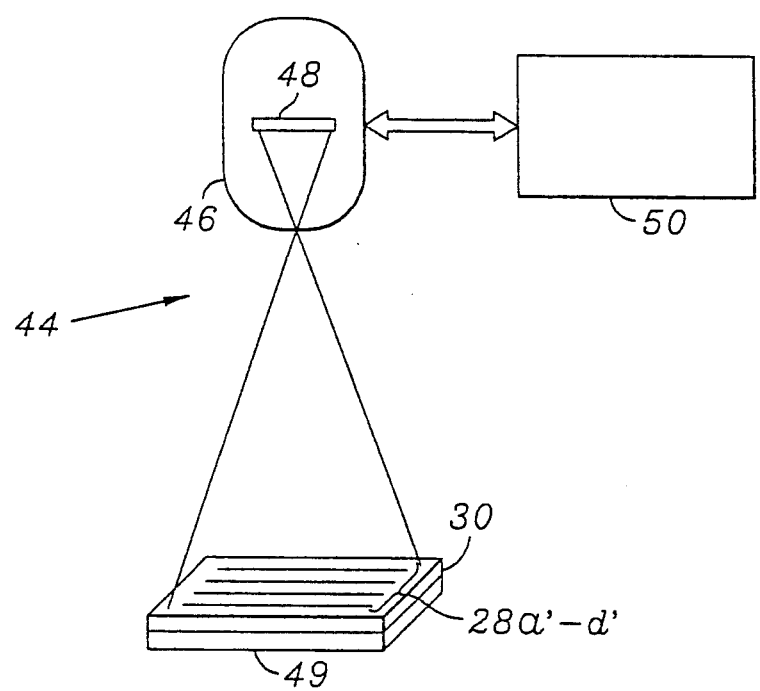
FIG. 4 is a schematic representation of a conventional charge-coupled device camera system utilized to image scintillation from the radioisotope-labeled sample components in capillaries.

Scintillation detection using CCD imagers typically requires several hours of exposure of the separated components. The present invention provides a technique for maintaining the components in their separated state during this long exposure period i.e. by maintaining the capillary section containing the separated components in a frozen state. Hence the present invention makes possible the use of CCD imaging systems for scintillation detection of components separated by a capillary electrophoretic process. Referring to FIG. 4, the use of a CCD camera system 44 is schematically shown. The camera head 46 focuses the image of the scintillations of the frozen sections 28a'–28d' of capillary tubes containing scintillators onto a CCD imager 48 to provide a quantitative analysis of the separated sample components. Throughout the CCD detection period, the capillary sections 28a'–d' are maintained in a frozen state. This can be accomplished for example by placing a peltier cooler 49 below the filter paper 30 or carrying out the detection in a refrigerated chamber. The conventional electronic control of the system 44 is represented by block 50.

When scintillation is contemplated, any non-transmissive exterior coatings should be removed before detection. It may be necessary to coat the external surface of the capillary tube with a material which is sufficiently transparent at the wavelength of the scintillation emission.

The advantages of the present invention can be readily appreciated. Compared to the flow counting approach, the detection technique of the present invention allows greater sensitivity without compromising resolution. An image of the spatial resolution of the separated sample components can be obtained either qualitatively or quantitatively, or both. Furthermore, from the image, one can locate a particular separated component within the separation channel for subsequent recovery of the component. Since the contents of the capillary should be maintained in their frozen state after separation, the capillary tube can be severed at locations bounding the desired separated component and the frozen component can subsequently be extracted from the severed section. Thus, the present invention provides a means of recovery of purified components.

While the invention has been described with respect to the illustrated embodiments in accordance therewith, it will be apparent to those skilled in the art that various modifications and improvements may be made without departing from the scope and spirit of the invention. For example, although the present invention has been illustrated with reference to an electrophoretic separation process, it is recognized that the detection technique of the present invention may be used with other types of separations employing capillary separation channels Furthermore, it is contemplated that a cooling device such as a peltier element may be provided in the system shown in FIG. 1 for freezing a section of the capillary tube containing the separated components. The detector used in conventional flow counting detection can be moved along the frozen section to obtain an image representative of the relative amounts of the separated components.

Accordingly, it is to be understood that the invention is not to be limited by the specific illustrated embodiments, but only by the scope of the appended claims.

We claim:

1. A method for analyzing radioisotope labeled components carried in a separation medium in a capillary, the method comprising the steps of:
   electrophoretically separating the components;
   freezing a section of the capillary containing the components; and
   analyzing the components while they are held in the frozen section.

2. A method as in claim 1 wherein the analyzing step comprises:
   placing the section of the capillary containing the components in proximity to a radiation sensitive imaging means; and
   exposing the imaging means to the section of the capillary so as to obtain an image representative of the relative amounts of the components.

3. A method as in claim 3 wherein the separation medium comprises a stabilizing gel.

4. A method as in claim 2 wherein the imaging means comprises an X-ray film.

5. A method as in claim 2 wherein the imaging means comprises a photographic film.

6. A method as in claim 5 further comprising the step of placing a scintillation material in proximity to the separated components, the scintillation material emitting photons in response to radiation from the separated components.

7. A method as in claim 2 wherein the imaging means comprises a solid state imager which is responsive to incident photons.

8. A method as in claim 7 further comprising the step of placing a scintillation material in proximity to the separated components, the scintillation material emitting photons in response to radiation from the separated components.

9. A method as in claim 8 wherein the solid state imager is a charge-coupled device which is responsive to photons to produce an electronic image of the radioactivity of the separated components for quantitative analysis.

10. A method for capillary electrophoretic separation of a sample in a capillary and analyzing the results thereof comprising the steps of:
    labeling the sample with a radioisotope;
    performing electrophoretic separation of the labeled sample into its components in a separation medium, each component being labeled with the radioisotope;
    freezing a section of the capillary containing the separated components; and
    analyzing the separated components while they are held in the frozen section.

11. A method as in claim 10 wherein the analyzing step comprises:
    placing the section of the capillary containing the radioisotope labeled components in proximity to a radiation sensitive imaging means; and
    exposing the imaging means to the section of the capillary containing the radioisotope labeled components so as to obtain an image representative of the relative amounts of the separated components.

12. A system for electrophoretic separation of a sample which comprises a plurality of components and analysis of the separated component thereof, the system comprising:
    a capillary tube containing the sample to be separated in a separation medium;
    means for radioisotope labeling the sample;
    means for separating the sample into its components electrophoretically, the components being radioisotope labeled;
    means for freezing a section of the capillary tube containing the separated components after electrophoretic separation; and
    analyzing means for analyzing the separated components while they are held in the frozen section.

13. A system as in claim 12 wherein the analyzing means comprises imaging means responsive to radiation from the radioisotope labeled components for imaging the section of the capillary tube containing the radioisotope labeled components and obtaining an image representative of the relative amount of the separated components.

14. A system as in claim 13 wherein the separation me comprises a stabilizing gel in the capillary tube.

15. A system as in claim 13 wherein the imaging means comprises an X-ray film.

16. A system as in claim 13 wherein the imaging means comprises a photographic film.

17. A system as in claim 16 further comprising a scintillation material placed in proximity to the separated components, the scintillation material emitting photons in response to radiation from the separated components.

18. A system as in claim 13 wherein the imaging means comprises a solid state imager which is responsive to incident photons.

19. A system as in claim 18 further comprising a scintillation material placed in proximity to the separated components, the scintillation material emitting photons in response to radiation from the separated components.

20. A system as in claim 19 wherein the solid state imager is a charge-coupled device which is responsive to photons to produce an electronic image of the radioactivity of the separated components for quantitative analysis.

21. In a system for separation of a sample into its components which are labeled with radioisotope in a buffer solution within a capillary separation channel, the detection and analysis of the result thereof using a device comprising means for freezing a section of the separation channel containing the separated components; and a means for detecting the separated components while they are held in the frozen section.

* * * * *